United States Patent [19]
Precetti et al.

[11] Patent Number: 5,979,252
[45] Date of Patent: Nov. 9, 1999

[54] SCALEABLE STATIC SAMPLE DIVIDER

[75] Inventors: Cyrille J. Precetti; James W. Stevenson; Michael E. Hartman, all of Des Moines, Iowa

[73] Assignee: Pioneer Hi-Bred International, Inc., Des Moines, Iowa

[21] Appl. No.: 09/074,891

[22] Filed: May 8, 1998

[51] Int. Cl.[6] .................................................. G01N 1/04
[52] U.S. Cl. ........................................................ 73/863.51
[58] Field of Search ............ 73/863.33, 863.41–863.43, 73/863.51, 863.52

[56] References Cited

U.S. PATENT DOCUMENTS

| | | |
|---|---|---|
| 518,915 | 4/1894 | Clarkson . |
| 573,610 | 12/1896 | Moore . |
| 2,379,921 | 7/1945 | Pizzirani et al. ...................... 73/863.43 |
| 2,405,486 | 8/1946 | Bauer . |
| 2,627,751 | 2/1953 | Pazandak . |
| 3,472,079 | 10/1969 | Cordell ................................ 73/863.51 |
| 3,512,418 | 5/1970 | Broman, Jr. ......................... 73/863.58 |
| 3,942,388 | 3/1976 | Rathnow et al. . |
| 4,524,628 | 6/1985 | Knudtson et al. . |
| 4,672,856 | 6/1987 | Marrs et al. ........................ 73/863.52 |
| 4,771,641 | 9/1988 | Beltrop et al. . |
| 5,426,987 | 6/1995 | Sprenger . |

OTHER PUBLICATIONS

Gamet Brochure, Seedburo Equipment Company, Chicago, Illinois Grain Probes Catalog, Seedburo Equipment Company, Chicago, Illinois, pp. 552, 570 and 640, no date.
Grain Probes Catalog, Seedburo Equipment Company, Chicago, Illinois, pp. 28,32, 33, 36, 44, 45, no date.

*Primary Examiner*—Robert Raevis
*Attorney, Agent, or Firm*—Zarley, McKee, Thomte, Voorhees & Sease

[57] ABSTRACT

A static sample divider of the present invention is adapted to sample a flow of material such as seed. The sample divider includes a housing which encloses an upwardly facing cone disposed above one or more sample cups. The sample cups are coupled to a sample receiving tube. When a flow of material is directed toward the cone, the cone spreads the flow of material radially and outwardly where a portion is caught by the sample cups and dumped into the sample receiving tube. The remainder of the material is discharged through a discharge tube. The sample cups can be removed and replaced with different numbers or different sizes of sample cups to control the proportion of material sampled.

15 Claims, 8 Drawing Sheets

SCALEABLE STATIC SAMPLE DIVIDER

BACKGROUND OF THE INVENTION

1. Field of the Invention

The present invention relates to sample dividers. More particularly, though not exclusively, the present invention relates to an apparatus and method for sampling a portion of a flowable material.

2. Problems in the Art

There are various needs for accurately obtaining representative samples of materials. For example, in the hybrid seed industry, samples of harvested seed are tested in laboratories for various reasons.

In one example prior art system, hybrid seed corn is shelled and a sample of fifty bushels of seeds is taken using some sort of flow diverter. The fifty bushel sample can then be shipped to a seed laboratory for sampling and testing. Smaller samples can be taken from the fifty bushel sample using prior art items such as sampling probes. A typical sampling probe is comprised of an open ended tube which is pressed into a bin of seed and removed to obtain a representative sample of the seed in the bin.

Various other prior art devices for collecting a sample of material are known in the art. Some prior art devices include a cone positioned in a flow of material for directing the flow of material across the surface of the cone. The device may also have a number of splitters for removing a sample from the material. Other devices use a series of staged funnels with the lowermost funnel having chutes for removing a portion of the material from the stream. The prior art devices have various disadvantages. First, many of the prior art sampling devices require the use of a motor which increases the cost and complexity of the device. In addition, prior art sampling devices cannot handle high capacity, but rather are intended for use in a laboratory where a small amount of material flow is sampled.

Another problem with prior art sample dividers relates to their flexibility. Prior art sample dividers are typically very limited in the selectability of the ratio to be sampled.

3. Features of the Invention

A general feature of the present invention is the provision of a method and apparatus for splitting a stream of material into different proportions which overcomes problems found in the prior art.

A further feature of the present invention is the provision of a method and apparatus for splitting a stream of material into different proportions in which the proportion is adjustable by the user.

A further feature of the present invention is the provision of a method and apparatus for splitting a stream of material into different proportions which uses modular dividers which can be put together to further split the material.

Further features, objects and advantages of the present invention include:

A method and apparatus for splitting a stream of material which uses a plurality of sample cups of differing sizes so that the split proportion can be selected by the user.

A method and apparatus for splitting a stream of material which includes a plurality of cones having different physical characteristics so that the user can select from the plurality of cones.

A method and apparatus for splitting a stream of material using modular splitters which can be stacked for further splitting the stream of material.

A method and apparatus for splitting a stream of material which includes a sample receiving tube which may be divided into a plurality of sections.

A method and apparatus for statically splitting a stream of material into different proportions.

A method and apparatus for splitting a stream of material which is capable of allowing a user to divide the flow accurately in a desired ratio.

These as well as other features, objects, and advantages of the present invention will become apparent from the following specification and claims.

SUMMARY OF THE INVENTION

The static sample divider of the present invention is used to divide or take a sample from a flow of material. The invention is comprised of a sample spreading member, such as a cone, for receiving the stream of material and spreading the stream in a plurality of directions. One or more sample cups is disposed below the sample spreading member for catching a portion of the stream of material. The sample receiving tube is in communication with the sample cup and receives the sampled portion of the stream of material. The present invention may optionally include a plurality of interchangeable sample cups so that the user can select the proportion of the sampled material by changing the size or number of sample cups. The sample divider may also be stacked with other similar sample dividers to further divide a flow of material.

DETAILED DESCRIPTION OF THE PREFERRED EMBODIMENT

The present invention will be described as it applies to its preferred embodiment. It is not intended that the present invention be limited to the described embodiment. It is intended that the invention cover all alternatives, modifications, and equivalencies which may be included within the spirit and scope of the invention.

Figure 1:
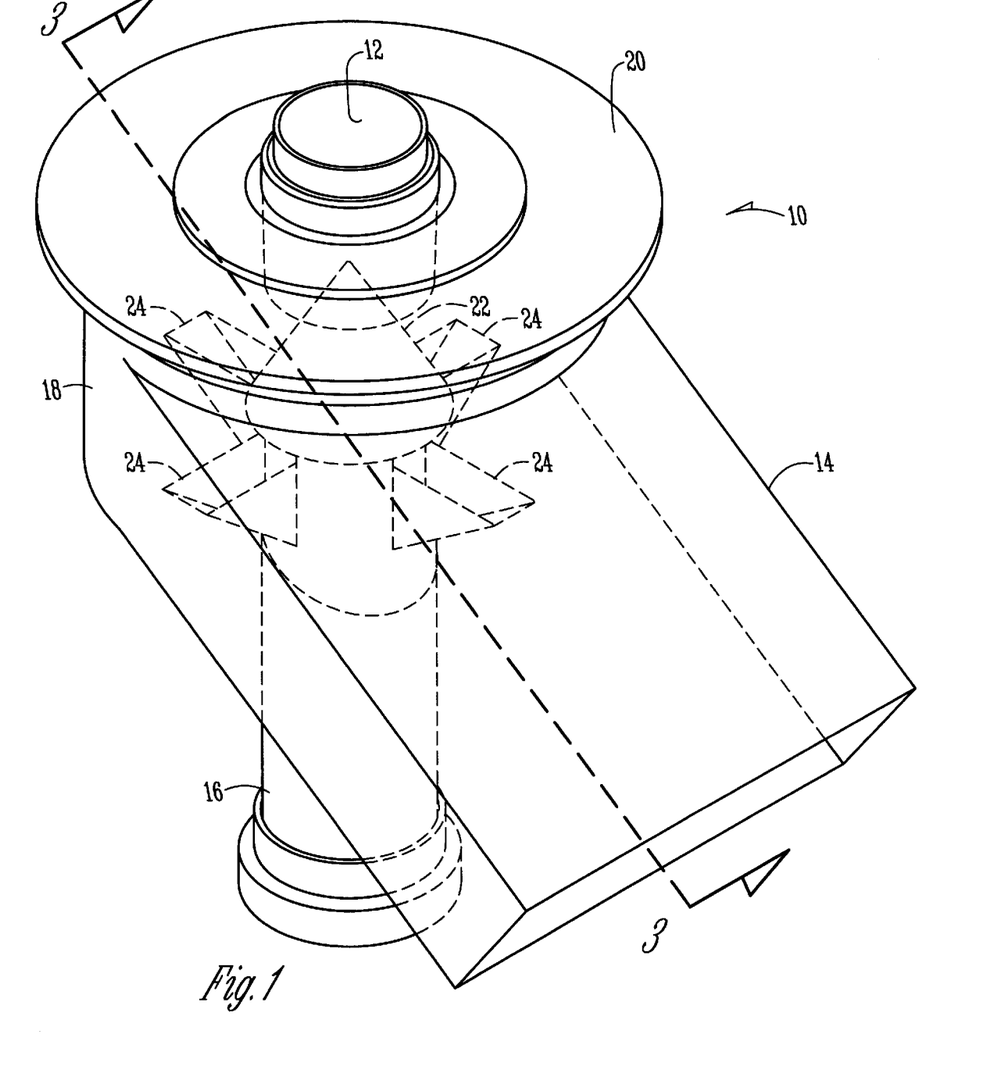
FIG. 1 is a perspective view of the sample divider according to the present invention.

FIG. 1 shows a modular sample divider 10 of the present invention. The sample divider 10 includes an intake tube 12, a discharge tube 14, and a sample receiving tube 16. When a stream of material, such as seed, flows into the intake tube 12, a portion of the seed will flow out of the discharge tube 14 and a portion of the seed will flow out of the sample receiving tube 16.

Figure 2:
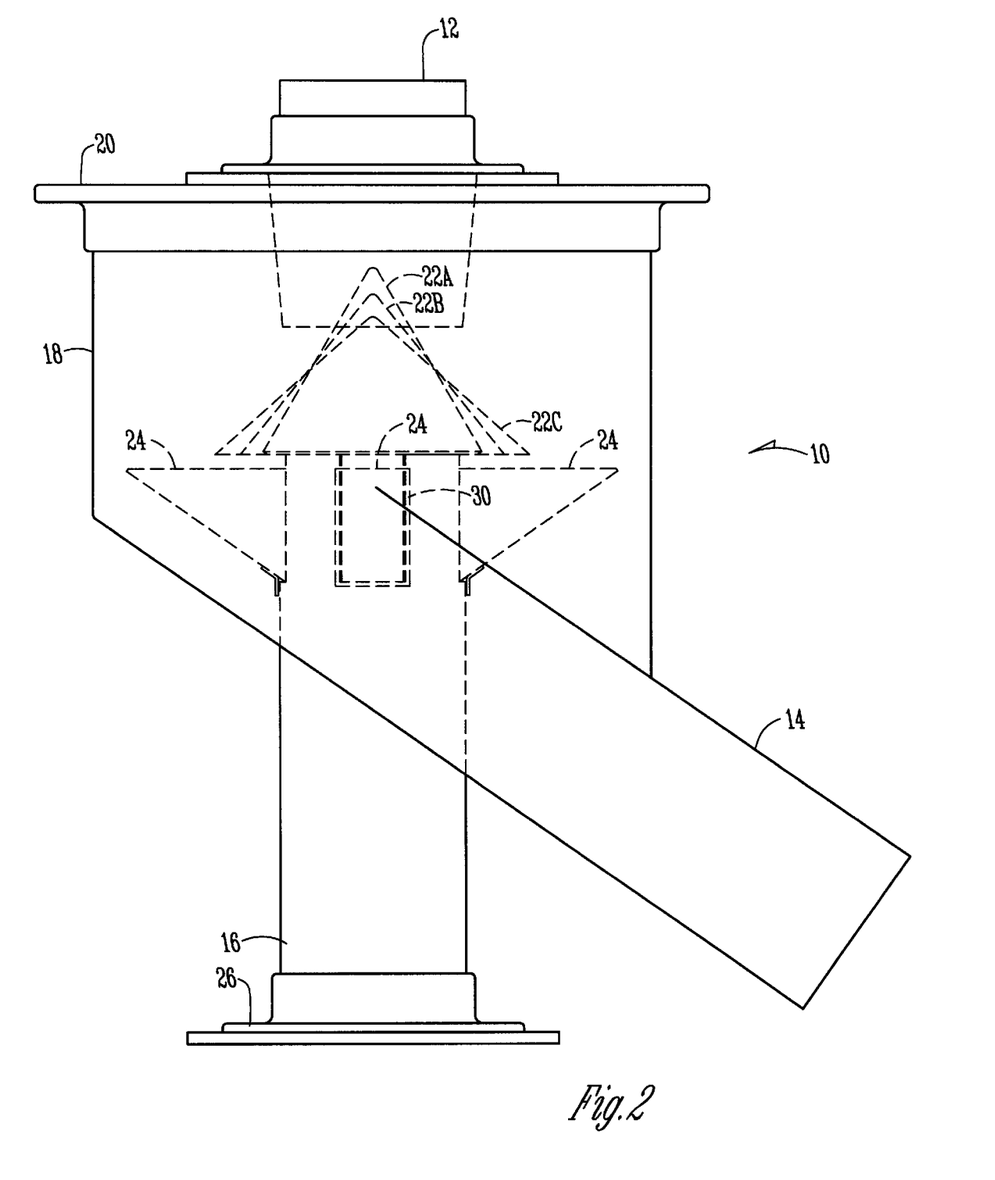
FIG. 2 is a side view of the sample divider shown in FIG. 1.

FIG. 2 is a side view of the modular sample divider 10 shown in FIG. 1. As shown, the sample divider 10 includes a housing 18 which houses the various components of the divider 10. A cover member 20 is disposed above the housing 18 and also serves to enclose the components of the sample divider 10. The intake tube 12 extends downward through the cover 20 and into the housing 18 as shown by dashed lines in FIG. 2. Disposed below the intake tube 12 is an upwardly facing cone 22. The cone 22 is coupled to and disposed above the sample receiving tube 16 as shown. FIG. 2 shows three alternate cones 22A, 22B, and 22C, each having a different slope. A user may choose between several cones 22 depending on factors such as the type of material being sorted. Since different materials may bounce off of surfaces differently, cones of various slopes may be needed. In addition, the cones 22 may have different textured surfaces. The cone 22 may take on many other shapes other than those shown in the Figures, for example, a pyramid shape, a spherical or oval shape, etc. Disposed around the periphery of the cone 22 are a plurality of sampling cups 24. The example shown in FIGS. 1 and 2 includes four sample cups 24. The sample cups 24 have an open upper end and an open side which is in communication with the inside of the sample receiving tube 16. In this way, any material that falls into the sample cups 24 flow into the sample receiving tube 16.

Figure 8:
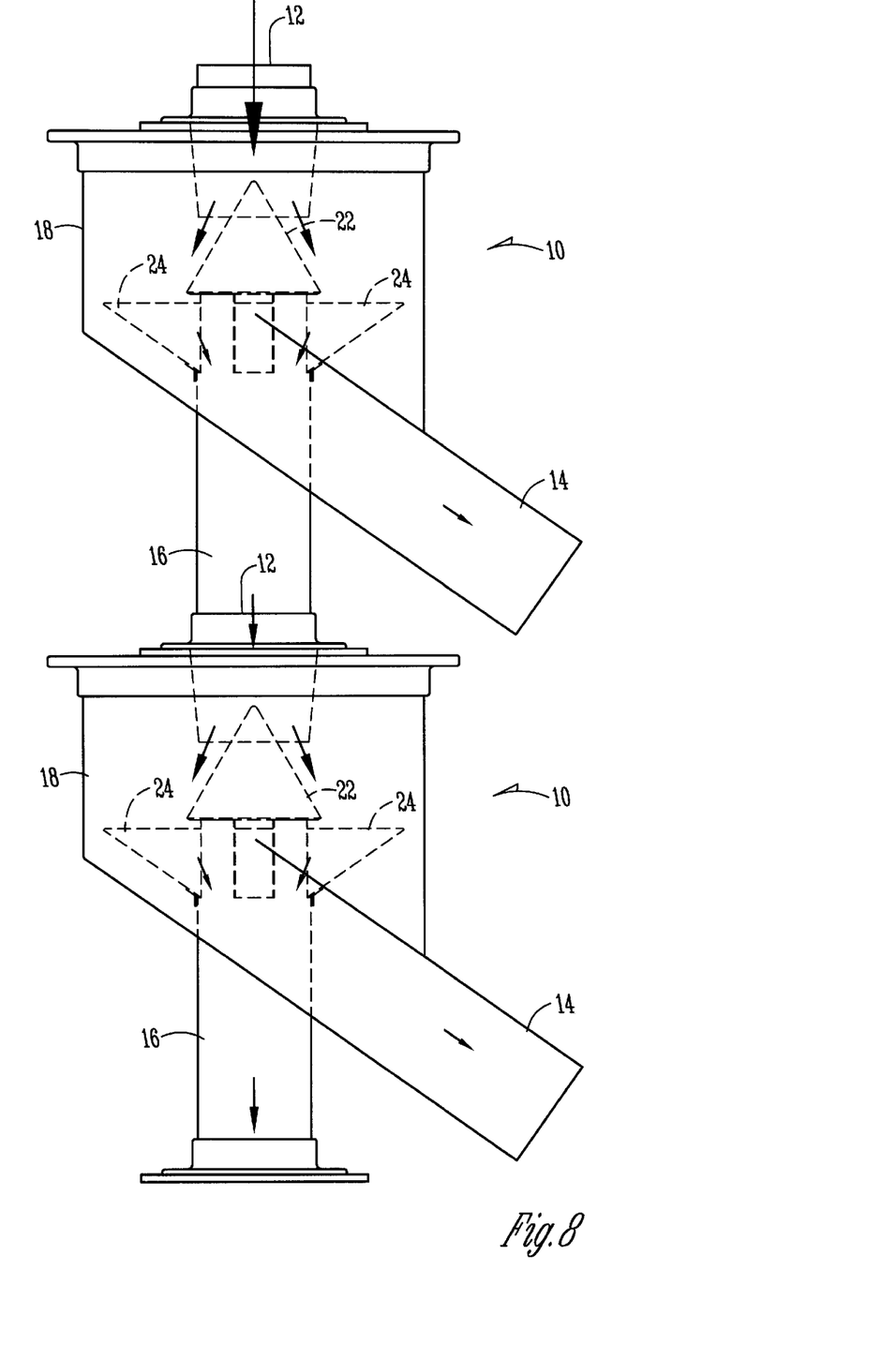
FIG. 8 is a side view of two modular sample dividers of the present invention stacked together.

The discharge tube 14 is formed in the housing 18 as shown. In the preferred embodiment, the discharge tube 14 has a rectangular cross section and slopes downward. In this way, the material flowing over the cone 22 which is not captured by the sample cups 24 will flow out of the discharge tube 14. A base 26 is coupled to the sample receiving tube 16 as shown in FIG. 2. The base 26 can be bolted to a surface or attached to another modular sample divider 10 as described below (FIG. 8).

Figure 3:
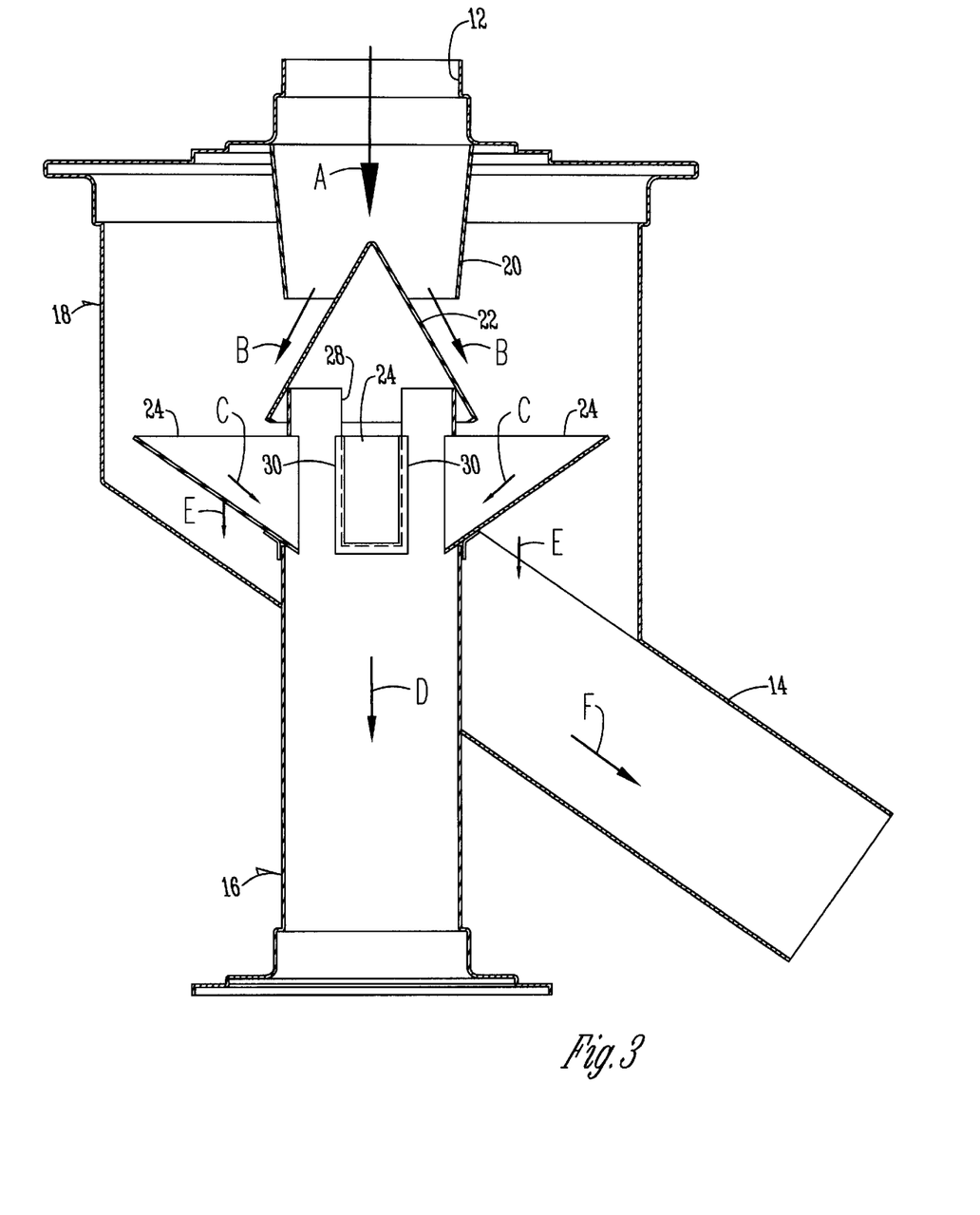
FIG. 3 is a sectional view taken along line 3—3 of FIG. 1.

FIG. 3 is a sectional view of the sample divider 10 showing the flow of material through the sample divider 10 (described in detail below). When a stream of material is fed into the intake tube 12, the cone 22 will spread or divide the flow of material radially and evenly. As the stream of material flows down the cone 22, the sampling cups 24 will catch a portion of the stream of material. The portion of material that is caught by the sample cups 24 will flow downward into the sample receiving tube 16 and into a sample bag or other container. The portion of material which is not caught by the sample cups 24 will fall past the sample cups 24 and into the discharge tube 14 where the material will be received by a bag or other container.

Figure 4:
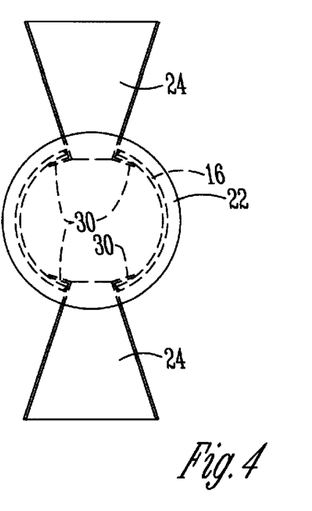
FIG. 4 is a top view of the sample receiving tube and sample cups of the present invention.
Figure 5:
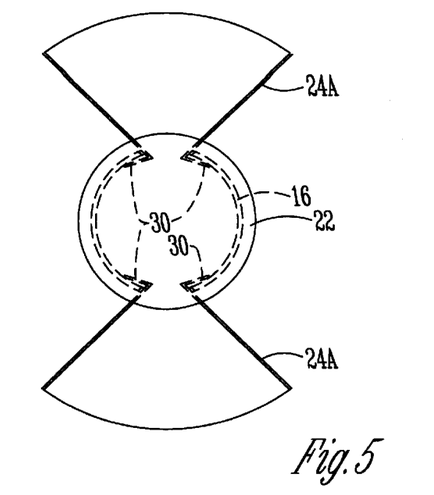
FIG. 5 is an alternative embodiment of the sample cups shown in FIG. 4.
Figure 6:
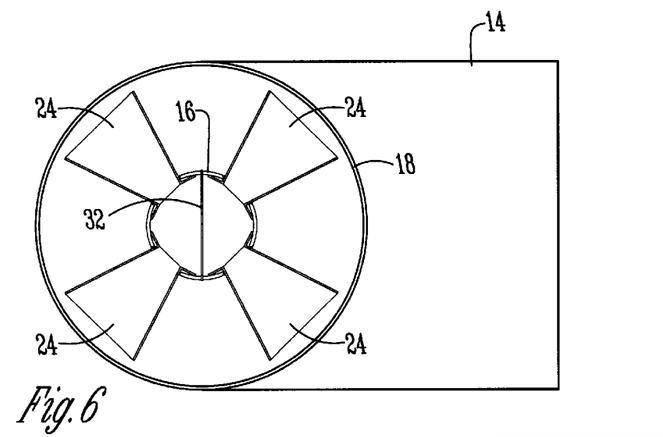
FIGS. 6 and 7 show top views of the sample divider of the present invention with the cover and cone removed and showing two alternate embodiments of the sample receiving tube.
Figure 7:
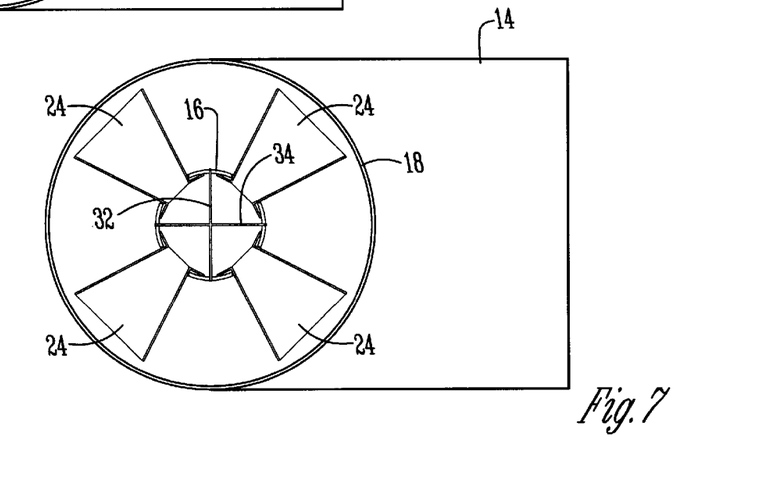

The modular sample divider 10 of the present invention is very flexible. The proportion of material caught by the sample cups 24 and received by the sample receiving tube 16 can be easily selected by a user. By changing the size or number of sample cups 24, more or less of the stream of material can be caught by the sample cups 24. FIGS. 4 and 5 show two alternate sized sample cups 24 and 24A attached to the sample receiving tube 16 below the cone 22. As shown, the sample cups 24A are larger than the sample cups 24 shown in FIG. 4 so that the proportion of material received by the sample receiving tube will be greater by using the sample cups 24A. FIGS. 4 and 5 show the use of two sample cups while FIGS. 6 and 7 show the use of four sample cups. As more sample cups 24 are used, the proportion received by the receiving tube 16 will increase. Any combination of numbers or sizes of sample cups 24 can be used with the present invention to give the user a very wide range of flexibility.

The sample cups 24 and 24A attach to the sample receiving tube 16 in the same manner so that the cups 24 and 24A are interchangeable. As shown in FIGS. 2 and 3, the sample receiving tube 16 includes a plurality of rectangular notches 28 which are adapted to receive the sample cups 24. The sample cups 24 have opposing flanges 30 which engage the inside surface of the sample receiving tube 16 to hold the sample cup 24 in place.

FIGS. 6 and 7 show two alternate embodiments of the present invention. The sample receiving tube 16 may optionally be divided into a plurality of passageways. FIG. 6 shows the sample receiving tube 16 with a divider 32 which divides the sample receiving tube 16 into two passageways. The sample receiving tube 16 can then be connected to two sample containing bags or other containers. In this way, the sample divider shown in FIG. 6 can simultaneously take two samples.

The sample divider 10 shown in FIG. 7 shows the sample receiving tube 16 with dividers 32 and 34 which divide the sample receiving tube 16 into four passageways. The sample receiving tube 16 can then be connected to four sample containing bags or other containers. In this way, the sample divider shown in FIG. 7 can simultaneously take four samples.

FIG. 8 shows two modular sample dividers 10 stacked together. As mentioned above, the base 26 of each sample divider 10 may be attached to the cover 20 of another modular sample divider 10. When a stream of materials is introduced into the intake tube 12 of the upper sample divider 10, the upper sample divider 10 will divide the stream of material as describe above. The portion of the material received by the sample receiving tube 16 of the upper sample divider 10 will be introduced into the intake tube 12 of the lower sample divider 10. The lower sample divider 10 then further divides the stream of material resulting in a smaller proportion of material flowing out of the sample receiving tube 16 of the lower sample divider 10. The embodiment of FIG. 8 provides the user with even more flexibility in choosing a sample proportion. For example, if the user chooses the number and size of sample cups 24 to provide a sampling ratio of 1/5 for both sample dividers 10, the resulting sample received by the sample receiving tube 16 of the lower sample receiving tube will be 1/25.

Figure 9:
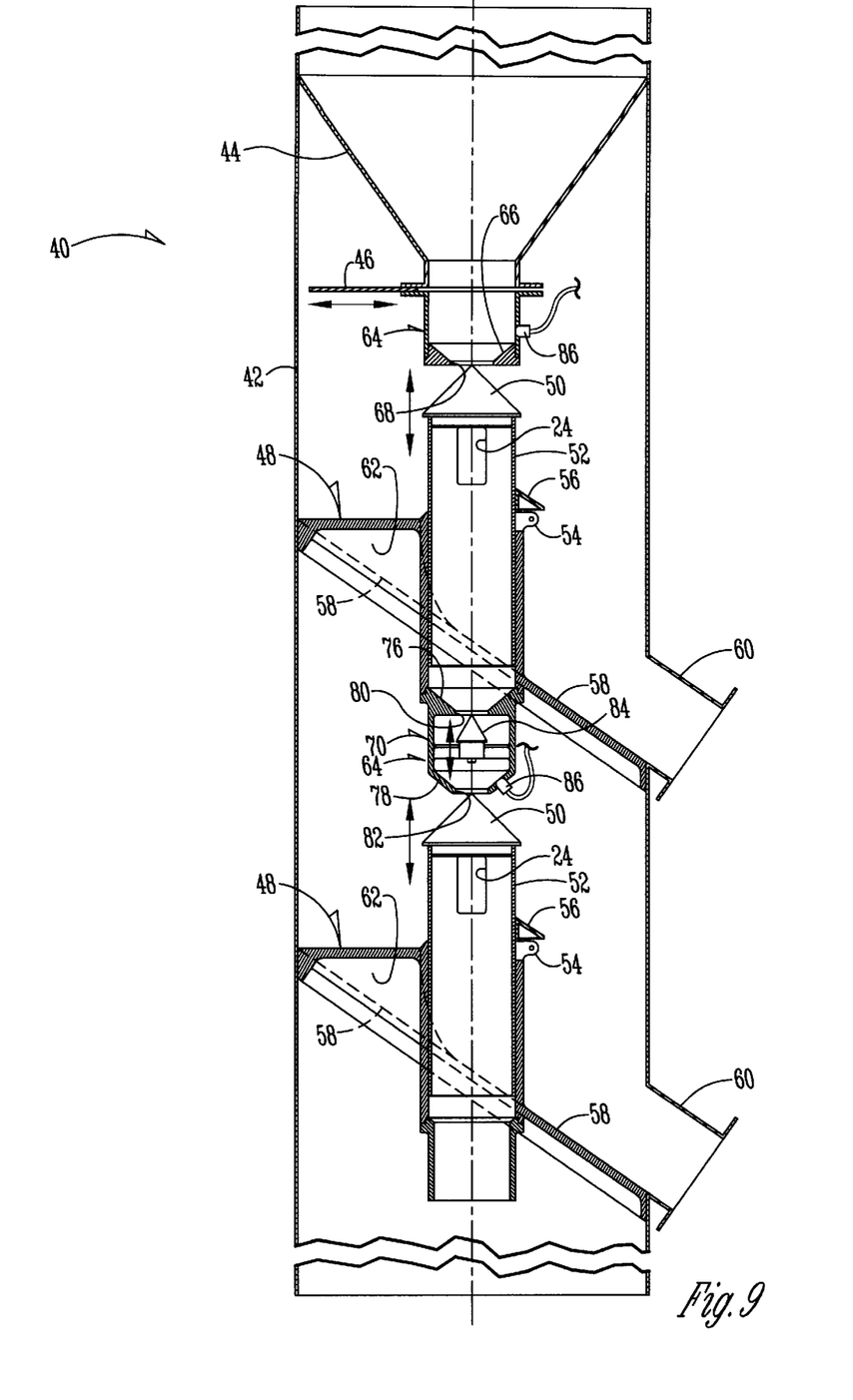
FIGS. 9 and 10 are sectional views of an alternate embodiment of the present invention.
Figure 10:
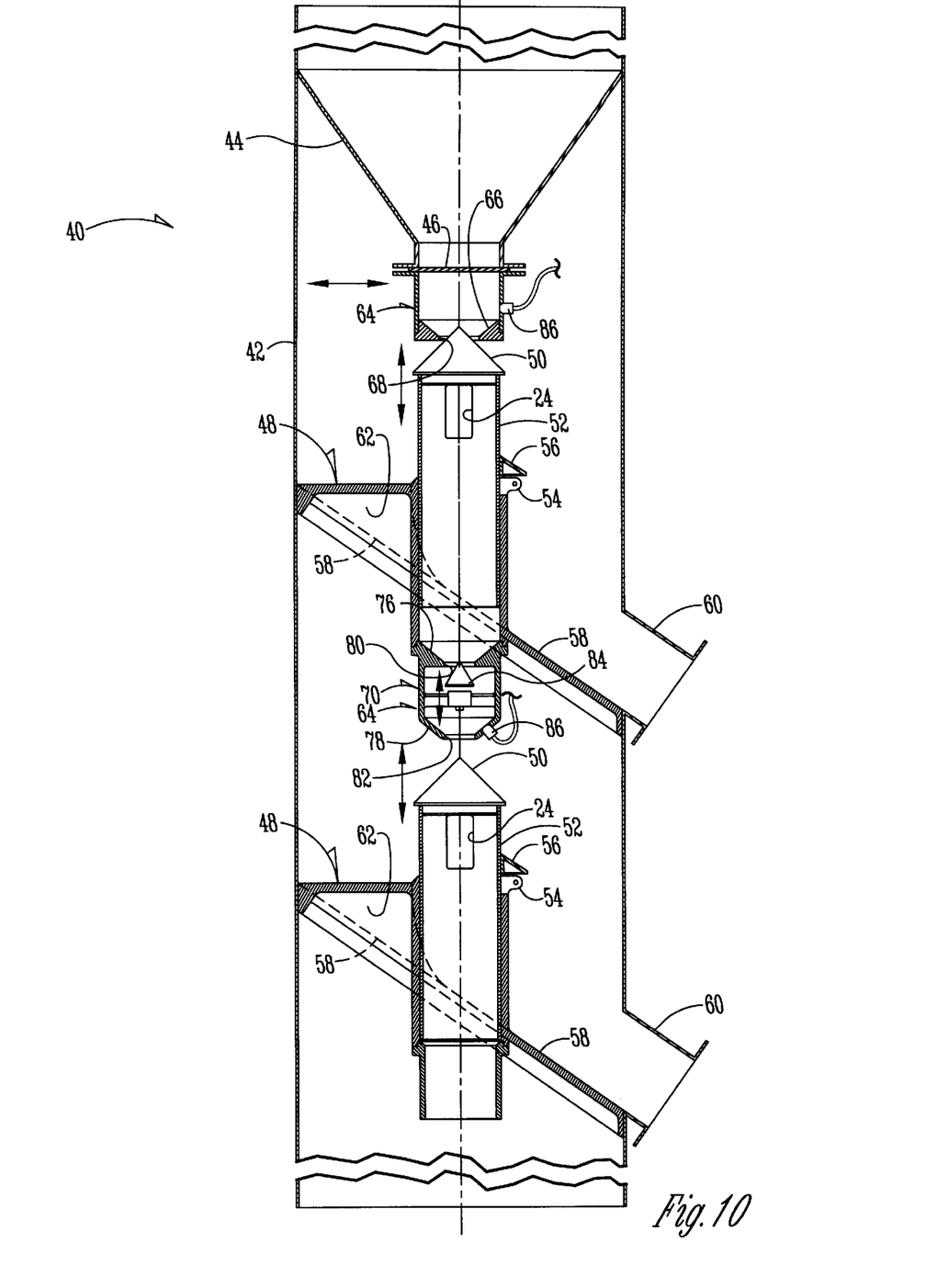

FIGS. 9 and 10 show an alternate modular sample divider 40. The sample divider 40 is enclosed in a square housing 42. At the top of the housing 42, a hopper 44 is formed to hold a quantity of material to be divided. A slide gate 46 is formed at the bottom of the hopper 44 to control the flow of material through the sample divider 40. Note that FIG. 9 shows the slide gate 46 open while FIG. 10 shows the slide gate 46 closed.

Secured within the housing 42 are two divider assemblies 48. FIG. 9 shows two divider assemblies 48, although one or more than two may be used together. Each divider assembly 48 includes a cone 50 and a sample receiving tube 52 similar to the cone 22 and tube 16 described above. Sample cups 24 are positioned around the tubes 52. The sample receiving tubes 52 are secured to the remainder of the divider assembly 48 by a clamp 54 which allows the tubes 52 to be adjusted up or down as indicated by the vertical arrows in FIGS. 9 and 10. FIGS. 9 and 10 show the tubes 52 is two different positions. A user may adjust the tubes 52 in order to position the cones 50 at different heights to accommodate different sized items which may be divided. Positioned above each clamp 54 is an angled deflector 56 which simply keeps particles from being caught on the clamp 54.

A slanted surface 58 is disposed as shown to catch and discharge material which is not caught by the cups 24. The slanted surfaces allow the material to be discharged through the discharge chutes 60 (similar to the discharge tubes 14). A pair of opposing slanted surfaces 62 slant downward to the slanted surface 58 to prevent material from getting caught against the back side of the tube 52.

When dividing certain materials, the materials will pick up speed as they fall through the hopper 44 and tubes 52. In order to slow the flow of material to a desired rate, a number of flow restrictors are used. A first flow restrictor 64 is placed below the hopper 44. The first flow restrictor 64 includes a slanted annular lip 66 which forms a restricted opening 68 above the cone 50. A second flow restrictor 70 is placed between adjacent divider assemblies 48. The second flow restrictor 70 includes an upper slanted annular lip 76 and a lower slanted annular lip 78 which form restricted openings 80 and 82, respectively. A restrictor cone 84 is disposed directly below the annular lip 76 and restricted opening 80. The combination of the annular lips 76 and 78 and the cone 84 restrict the flow of material through the divider 40 and reduce the speed of the material before it contacts the cone 50 on the divider assembly 48 below.

One potential problem with the restrictors 64 and 70 is that debris, such as corn stalks when dividing seed corn, may clog or bridge over the restricted openings 68, 80, or 82, causing the flow of material to stop. To overcome this problem, a source of compressed air is connected to air nozzles 86 mounted on the restrictors 64 and 70. Periodically (e.g., every 2 minutes, depending on the type of material being divided) a burst of air is blown through the nozzles 86 to dislodge any debris that may be blocking the flow of material.

The present invention operates as follows. The operation of the present invention will be described for use with a flow of seeds, although it is understood that the sample divider may be used for any number of materials. In addition, the operation will be described with respect to the embodiment of FIGS. 1–8. The user of the sample divider 10 first will determine by what ratio that the stream of seeds should be divided. The user can then choose the appropriate size and number of sample cups 24 to be used. By removing the cover 20 from the housing 18, the user will have access to the cups 24. After pulling off the cone 22, the sample cups 24 can be lifted upward out of the slots 28 of the sample receiving tube 16. The selected sample cups 24 can then be inserted into the slots 28. The cone 22 and cover 20 can then be replaced. Depending on the particular use, the user may attach a sample receiving bag or other suitable container to the sample receiving tube 16. Similarly, the user may attach any type of container to the discharge tube 14.

The user may then introduce a flow of material into the intake tube 12 (illustrated by arrow A in FIG. 3). As the stream of material hits the cone 22, the cone will divide the stream of material radially and evenly as shown by the arrows B in FIG. 3. A portion of the material will fall into the sample cups 24 and flow downward toward the sample receiving tube 16 as shown by the arrows C. The portion of material flowing into the sample receiving tube 16 will flow downward, as shown by the arrow D, until it is caught by a sample receiving bag or other container.

The portion of the stream of material which is not caught by the sample cups 24 (shown by the arrows E) will flow out of the discharge tube 14 as shown by the arrow F. The seed exiting the discharge tube 14 may be collected by a sample bag or other container or may be dumped back into a storage bin.

As discussed above, the user has various options in using the modular sample divider 10. Besides changing the number and the size of the sample cups 24, the user may choose between a number of cones 22. Depending on what the stream of material is comprised of, or other factors, cones having differing slopes or surface textures may be desired. In addition, the user can sample at a wider variety of ratios by combining a plurality of the sample dividers 10. As shown in FIG. 8, two sample dividers 10 are combined to provide a certain sample ratio. If the user desires, more than two sample dividers 10 may be combined in a manner similar to that shown in FIG. 8.

The user also has the option of choosing between a plurality of sample receiving tubes 16 such as those shown in FIGS. 4–7. If desired, the material received by the sample receiving tube 16 may be subdivided into more than one stream of material.

Figure 11:
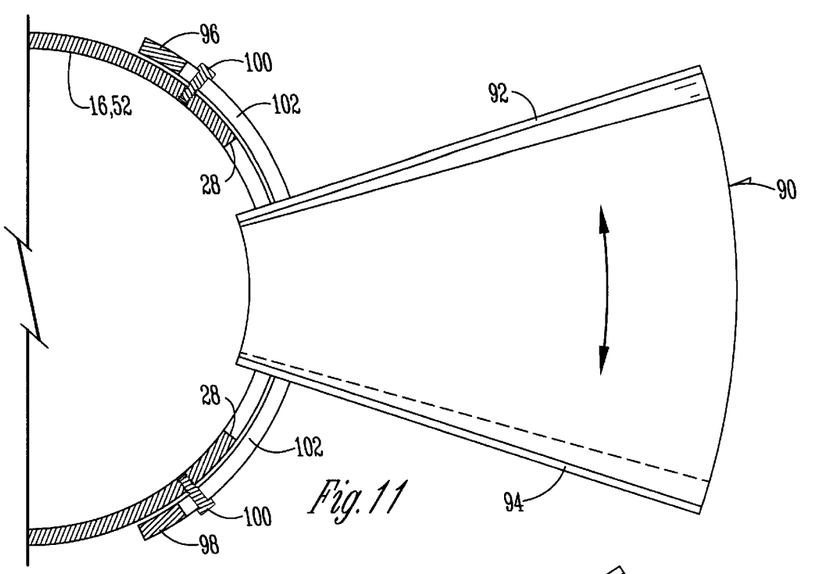
FIGS. 11 and 12 show adjustable sample cups.
Figure 12:
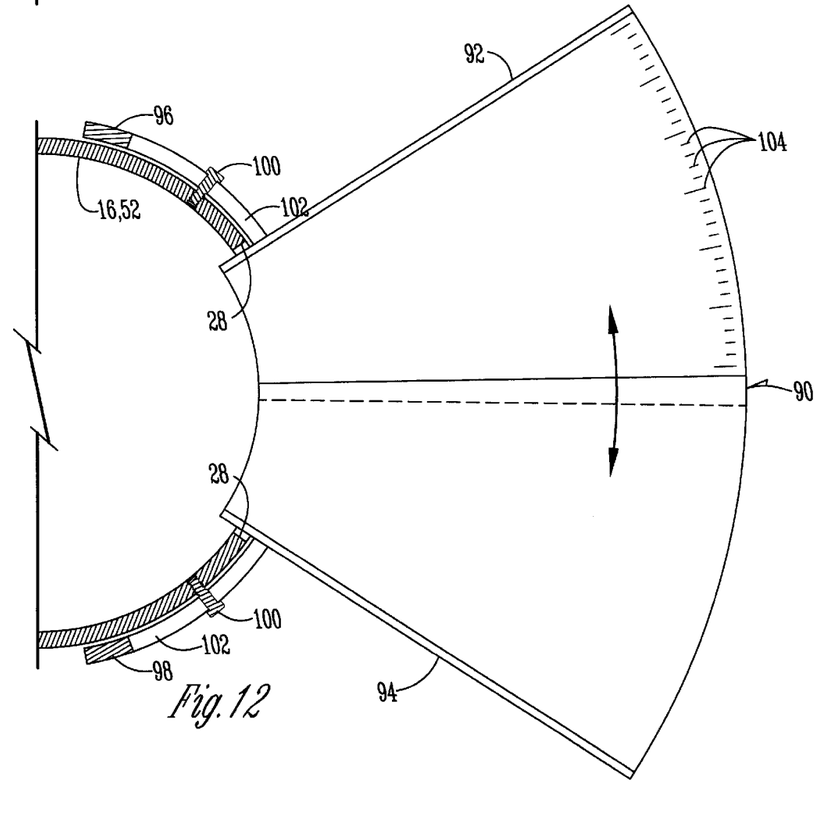

Other optional features include a device for cleaning the sample divider 10. A vacuum apparatus can be connected to the housing of the sample divider to vacuum dust and debris from the sample divider either during use or after use. In another optional embodiment, the housing 18 could have a hinged door to allow access to the sample cups. Also, the sample cups 24 could be adjustable in size so that a user could adjust the size of the cups without having to switch between a number of fixed-sized cups. FIGS. 11 and 12 show an adjustable sample cup 90. The cup 90 includes first and second halves 92 and 94. As shown, the second half 94 overlaps the first half 92 so that by moving the halves 92 and 94 in the directions of the arrows, the size of the cup 90 can be adjusted. The first half 92 is coupled to a first flange 96 while the second half 94 is coupled to a second flange 96. To secure the halves 92 and 94 in the desired position, the set screws 100 are tightened. The set screws 100 are each threaded into the tube 16 or 52 and pass through a slot 102 formed in the flanges 96 and 98. Indicia 104 may be formed on the surface of the half 92 to provide an indication of the size of the cup 92. Alternatively, discrete holes may be formed in the flanges 96 and 98 in place of the slots 102. In this way, the cup 90 would be adjustable in discrete increments.

The sample divider of the present invention is not limited to use with seed corn. The sample divider may be used with other particulate or non-particulate materials, such as plastic or metal pieces, or even liquids.

The preferred embodiment of the present invention has been set forth in the drawings and specification, and although specific terms are employed, these are used in a generic or descriptive sense only and are not used for purposes of limitation. Changes in the form and proportion of parts as well as in the substitution of equivalents are contemplated as circumstances may suggest or render expedient without departing from the spirit and scope of the invention as further defined in the following claims.

What is claimed is:

1. A method of sampling a desired proportion of a stream of material comprising:

positioning a sample spreading member in a substantially vertical flow of material to spread the stream of material in an outward direction, selecting the sample spreading member from a plurality of sample spreading members having differing slopes based on the type of material comprising the stream of material;

providing a plurality of sample cups having differing sizes;

selecting one or more of the plurality of sample cups based on the desired proportion;

placing the selected sample cups below the sample spreading member to collect a portion of the stream of material as the material flows down the sample spreading member;

directing the collected portion of the stream substantially vertically downward to an outlet; and discharging the uncollected portion of the stream generally outwardly and laterally above the outlet.

2. The method of claim 1 further comprising the step of providing a discharge tube for collecting the part of the stream of material not collected by the selected sample cups.

3. The method of claim 1 further comprising the step of providing a sample receiving tube disposed below the sample spreading member and being in communication with the selected sample cups for receiving the collected portion of the stream of material.

4. The method of claim 3 further comprising the steps of:

positioning a second sample spreading member below the sample receiving tube for spreading the flow of material received by the sample receiving tube; and placing one or more sample cups below the second sample spreading member to collect a sample of the portion of the stream of material flowing down the second sample spreading member.

5. The method of claim 3 wherein the selected sample cups are inserted into notches formed in the sample receiving tube.

6. A static sample divider for sampling a flow of material comprising:

a housing having side walls and a top;

an aperture formed in the top of the housing for receiving the flow of material;

a upwardly-facing cone disposed below the aperture for spreading radially the flow of material as the material flows down over the cone;

a sample receiving tube disposed below the cone and having a lower outlet;

at least one adjustable in size sample cup disposed below the cone and being in communication with the sample receiving tube for collecting a portion of the flow of material which flows down over the cone;

a discharge tube having a receiving section positioned around and underneath the sample cup for capturing and discharging the portion of the stream of material not caught by the sample cup, and having a discharge end in communication with the receiving section, the discharge end extending outside of and laterally above the outlet.

7. The static sample divider of claim 6 wherein the at least one sample cup is removably coupled to the static sample divider.

8. The static sample divider of claim 7 further comprising a plurality of sample cups, at least some of the sample cups having differing sizes, wherein one or more of the plurality of sample cups are coupled to the sample divider to control the sampled proportion of the flow of material.

9. The static sample divider of claim 6 wherein the sample divider is adapted to be stacked with a another static sample divider according to claim 6 for sampling the sampled material from the similar sample divider.

10. The static sample divider of claim 6 further comprising a flow restrictor disposed within the sample receiving tube to restrict the flow of material through the sample receiving tube.

11. The static sample divider of claim 10 further comprising an air nozzle positioned in the proximity of the flow restrictor to clear any clogs formed in the flow restrictor by blowing compressed air toward the flow restrictor.

12. A method of sampling a desired proportion of a stream of material comprising:

providing a plurality of sample spreading members having differing slopes;

selecting one of the plurality of sample spreading members based on the type of material comprising the stream of material;

positioning a said sample spreading member in the flow of material to spread the stream of material in an outward direction;

providing a plurality of sample cups having differing sizes;

selecting one or more of the plurality of sample cups based on the desired proportion; and placing the selected sample cups below the sample spreading member to collect a portion of the stream of material as the material flows down the sample spreading member.

13. A static sample divider for sampling a flow of material comprising:

a housing having side walls and a top;

an aperture formed in the top of the housing for receiving the flow of material;

a upwardly-facing cone disposed below the aperture for spreading radially the flow of material as the material flows down over the cone;

a sample receiving tube disposed below the cone; and at least one sample cup adjustable in size and disposed below the cone and being in communication with the sample receiving tube for collecting a portion of the flow of material which flows down over the cone.

14. A static sample divider for sampling a flow of material comprising:

a housing having side walls and a top;

an aperture formed in the top of the housing for receiving the flow of material;

a upwardly-facing cone disposed below the aperture for spreading radially the flow of material as the material flows down over the cone;

a sample receiving tube disposed below the cone;

a flow restrictor disposed within the sample receiving tube to restrict the flow of material through the sample receiving tube;

an air nozzle positioned in the proximity of the flow restrictor to clear any clogs formed in the flow restrictor by blowing compressed air toward the flow restrictor; and at least one sample cup disposed below the cone and being in communication with the sample receiving tube for collecting a portion of the flow of material which flows down over the cone.

15. A static sample divider for sampling a flow of material comprising:

a housing having side walls and a top;

an aperture formed in the top of the housing for receiving the flow of material;

a upwardly-facing cone disposed below the aperture for spreading radially the flow of material as the material flows down over the cone;

a sample receiving tube disposed below the cone and having a lower outlet;

at least one sample cup disposed below the cone and being in communication with the sample receiving tube for collecting a portion of the flow of material which flows down over the cone;

a discharge tube having a receiving section positioned around and underneath the sample cup for capturing and discharging the portion of the stream of material not caught by the sample cup, and having a discharge end in communication with the receiving section, the discharge end extending outside of and laterally above the outlet;

a flow restrictor disposed within the sample receiving tube to restrict the flow of material through the sample receiving tube; and an air nozzle positioned in the proximity of the flow restrictor to clear any clogs formed in the flow restrictor by blowing compressed air toward the flow restrictor.

* * * * *